United States Patent [19]

Kapp

[11] Patent Number: 4,763,645
[45] Date of Patent: Aug. 16, 1988

[54] TRACHEAL TUBE FILTER

[76] Inventor: Michael J. Kapp, 7 Fulton St., Freehold, N.J. 07728

[21] Appl. No.: 89,165

[22] Filed: Aug. 25, 1987

[51] Int. Cl.[4] .......................... A62B 7/10; A62B 23/02
[52] U.S. Cl. .............................. 128/205.29; 128/207.14
[58] Field of Search ....................... 128/200.26, 207.14, 128/207.15, 207.16, 207.17, 205.29, 205.27

[56] References Cited

U.S. PATENT DOCUMENTS

| | | | |
|---|---|---|---|
| 2,039,142 | 4/1936 | Brehm | 128/207.17 |
| 2,491,647 | 12/1949 | Colavita | 128/207.14 |
| 3,101,709 | 8/1963 | Gruenewaelder | 128/206.12 |
| 3,263,684 | 8/1966 | Bolton | 128/207.16 |
| 3,330,271 | 7/1967 | Hozier | 128/207.14 |
| 4,231,364 | 11/1980 | Speshyock | 128/207.14 |
| 4,325,366 | 4/1982 | Tabor | 128/207.16 |

Primary Examiner—William E. Kamm
Assistant Examiner—Timothy G. Philips
Attorney, Agent, or Firm—Jerry T. Kearns

[57] ABSTRACT

A filter for various types of tracheal tubes has a tubular filter holder which is inserted into or snapped onto the outer end of an existing tracheal tube. A fibrous filter which may be treated with a germicidal agent is received in the filter holder. A removable end cap having a filter screen is disposed on the end of the filter holder. In one embodiment, the filter holder is constructed integrally with the end cap, and disposable fibrous filters are utilized. The end cap may be constructed as a decorative jewelry item, and may be provided with a decorative strap or chain for wearing around the user's neck. The strap or chain also functions as a retainer for the filter holder.

8 Claims, 1 Drawing Sheet

TRACHEAL TUBE FILTER

BACKGROUND OF THE INVENTION

1. Field of the Invention

The present invention relates to tracheal tubes, and more particularly pertains to a new and improved filter for various types of tracheal tubes. The filter of the present invention is primarily intended for use with tracheostomy and laryngectomy tubes. A tracheostomy is generally performed on patients with an obstructed airway. While this procedure successfully provides an unobstructed airway for the patient, there are disadvantages associated with a tracheostomy. The new airway created by a tracheostomy bypasses the patient's nasal passages and the upper esophagus. The hairs and mucous of the nasal passages constitute a natural filtration system. Also, the mucous and cilia of the walls of the upper esophagus act to remove impurities from the air. Thus, as a result of a tracheostomy, the patient is deprived of the body's natural air filtration system. The present invention is directed to overcoming the aforementioned disadvantages of tracheostomy operations by providing an air filter for tracheostomy tubes. While primarily intended for use by patients with tracheostomy tubes, the filter of the present invention may also be used with endotracheal of larygectomy tubes.

A further disadvantage of tracheostomy operations on patients with permanently obstructed airways is that an unsightly tracheostomy tube is displayed on the patient's throat. Currently, many patients endeavor to hide the tube by wearing a scarf around their neck. This provides a partial obstruction of the patients airway. The present invention is directed toward the solution of this problem by providing an ornamented end cap for a tracheostomy tube which is worn as a jewelry item.

2. Description of the Prior Art

Various types of tracheal tubes are known in the prior art. A typical example of such a tracheal tube is to be found in U.S. Pat. No. 3,640,282, which issued to J. Kamen et al on Feb. 8, 1972. This patent discloses a resilient cuff for effecting an air seal between a tracheal tube and the patient's treachea. This sealing arrangement may be utilized with both endotracheal and tracheostomy tubes. U.S. Pat. No. 3,659,611, which issued to D. Miller on May 2, 1972, discloses a tracheal tube provided with sealing flanges for effecting an air seal between the tube and the trachea. These flanges are formed from a thin silicon rubber material. U.S. Pat. No. 4,155,365, which issued to R. Boslau on May 22, 1979, discloses an endotracheal tube having an expandable bladder for sealing the esophagus against air loss. U.S. Pat. No. 4,315,505, which issued to N. Crandall et al on Feb. 16, 1982, discloses a tracheostomy tube which has an outer cannula and a removable, disposable inner cannula. The inner cannula is provided with an air seal for preventing air flow between the inner cannula and the outer cannula. A coupling arrangement is provided to secure the inner cannula within the outer cannula. U.S. Pat. No. 4,526,196, which issued to J. Pistillo on July 2, 1985, discloses a pressure measuring and regulating device for use with a pressurized sealing cuff of an endotracheal or tracheostomy tube. A microporous membrane filter is provided.

While the above mentioned devices are suited for their intended usage, none of these devices discloses an easily changeable filter for a tracheal tube. Further, none of these devices discloses an ornamental end cap in combination with a tracheal tube filter. Inasmuch as the art is relatively crowded with respect to these various types of tracheal tubes, it can be appreciated that there is a continuing need for and interest in improvements to such tracheal tubes, and in this respect, the present invention addresses this need and interest.

SUMMARY OF THE INVENTION

In view of the foregoing disadvantages inherent in the known types of tracheal tubes now present in the prior art, the present invention provides an improved tracheal tube. As such, the general purpose of the present invention, which will be described subsequently in greater detail, is to provide a new and improved tracheal tube which has all the advantages of the prior art tracheal tubes and none of the disadvantages.

To attain this, representative embodiments of the concepts of the present invention are illustrated in the drawings and make use of a tubular filter holder adapted to be inserted into an outer end portion of a tracheal tube. Replaceable filter elements which are treated with a germicidal agent may be removably received in the tubular filter holder. The present invention further provides an ornamental end cap for the tubular filter holder, which is worn as a jewelry item. A removable screen is retained in the end cap.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved tracheal tube filter which has all the advantages of the prior art tracheal tubes and none of the disadvantages.

It is another object of the present invention to provide a new and improved tracheal tube filter which may be easily and efficiently manufactured and marketed.

It is a further object of the present invention to provide a new and improved tracheal tube filter which is of a durable and reliable construction.

An even further object of the present invention is to provide a new and improved tracheal tube filter which is susceptible of a low cost of manufacture with regard to both materials and labor, and which accordingly is then susceptible of low prices of sale to the consuming public, thereby making such tracheal tubes economically available to the buying public.

Still yet another object of the present invention is to provide a new and improved tracheal tube filter which provides in the apparatuses and methods of the prior art some of the advantages thereof, while simultaneously overcoming some of the disadvantages normally associated therewith.

Still another object of the present invention is to provide a new and improved tracheal tube filter which is disposable or which provides easily changeable, disposable filter elements.

Yet another object of the present invention is to provide a new and improved tracheal tube filter which provides an ornamental end cap.

Even still another object of the present invention is to provide a new and improved tracheal tube filter having an ornamental end cap with a replaceable screen.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
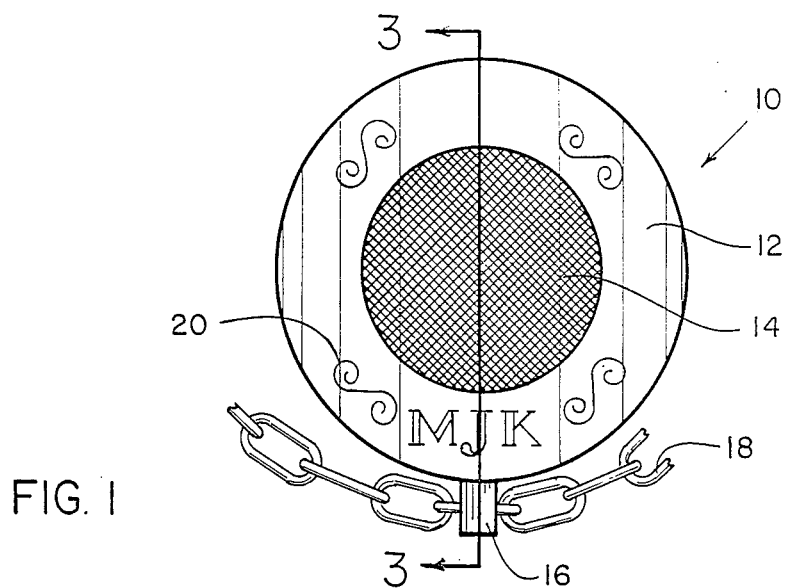
FIG. 1 is a front view of tracheal tube filter end cap of a first embodiment of the present invention.

With reference now to the drawings, and in particular to FIG. 1 thereof, a new and improved tracheal tube filter embodying the principles and concept of the present invention and generally designated by the reference numeral 10 will be described.

More specifically, it will be noted that the first embodiment 10 of the invention includes an end cap 12 having a central aperture across which is mounted a screen 14. The end cap 12 may be formed of autoclavable plastic, stainless steel, silver or other precious metals. The screen 14 is preferably a microporous membrane formed from a resilient material. A chain loop 16 is formed on end cap 12, and a chain 18 is disposed therethrough. The chain 18 is adapted to be worn around the neck of an individual, and serves as ornamentation and as a safety chain for the retention of end cap 12. The end cap 12 may be provided with ornamentation such as the wearer's initials or engraving 20. It is also contemplated that a design, such as a cameo, may be provided on the screen 14. Then, straps may be substituted for the chain 18, and the tracheal tube filter 10 will resemble a cameo when worn by a female. Other ornamental designs may be substituted for those described above; the concept of the present invention is to provide an ornamental end cap.

Figure 2:
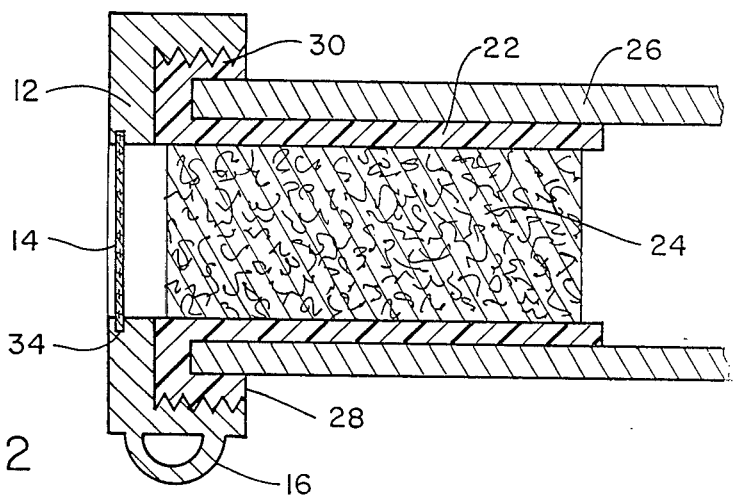
FIG. 2 is a cross sectional view of a first embodiment of a traacheal tube filter of the present invention, taken along lines 2—2 of FIG. 1.

With reference now to FIG. 2, the construction of the tracheal tube filter 10 will be described. A tubular filter holder 22 having a fibrous filter 24 disposed therein is inserted into an outer end portion of a tracheal tube 26. The tubular filter holder 22 has an integrally formed lip 28. The lip 28 forms a circular annular recess which is received over the outer end portion of the tracheal tube 26. Threads 30 are formed on an outer cylindrical surface of the lip 28. The end cap 12 has a circular recess provided with cooperating threads for engagement with the threads 30 of the lip 28. The end cap 12 has a circular undercut recess 34 for the reception of the screen 14. The tubular filter holder 22 may be constructed of plastic, stainless steel or the like, but is preferably constructed of a plastic material having some resiliency. This resiliency enables the lip 28 to be retained by frictional engagement over the outer end portion of the tracheal tube 26. The screen 14 has a sufficient resiliency to enable insertion into recess 34. The end cap 12 is preferably constructed of an ornamented precious metal, such as silver. The tubular filter holder 22 along with fibrous filter 24 constitutes a disposable filter unit. Screen 14 may be designed as a disposable element, or may be removed and cleaned.

Figure 3:
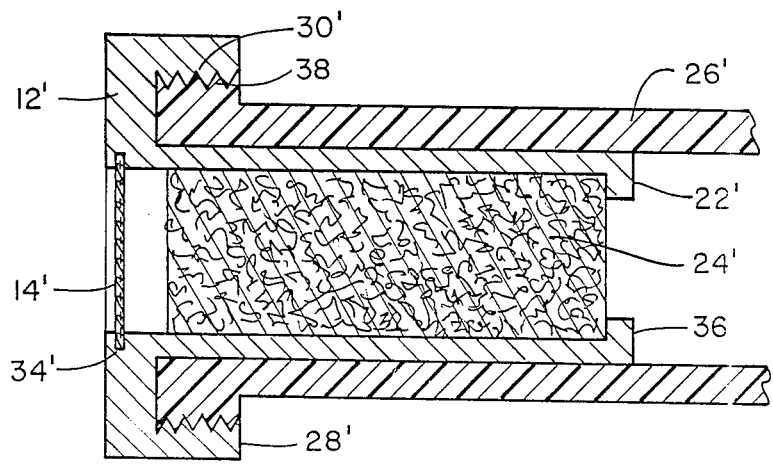
FIG. 3 is a cross sectional view of a second embodiment of a tracheal tube filter of the present invention.

With reference now to FIG. 3, a second embodiment of a tracheal tube filter according to the present invention will be described. A tubular filter holder 22' having a circular retaining flange 36 is disposed within an outer end portion of a tracheal tube 26'. The tracheal tube 26' is of the type having a cylindrical outer surface provided with threads 38. The tubular filter holder has an integrally formed lip 28' forming an annular recess provided with threads 30' on the inner wall of the recess for cooperative engagement with the threads 38 of the tracheal tube 26'. A disposable fibrous filter 24', which may be treated with a conventional germicidal agent which is effective in reducing nosocomical infections, is removably received within the tubular filter holder 22'. An end cap 12' is formed integrally with the tubular filter holder 22' and lip 28'. A screen 14' having a circular peripheral edge is removably retained in a circular undercut recess 34' in the end cap 12'. In this embodiment, it is contemplated that end cap 12', lip 28' and tubular filter holder 22' will be formed of stainless steel or a precious metal such as silver. Ornamentation such as that shown in FIG. 1 may be provided along with an ornamental chain or strap. In this embodiment, a safety retaining chain or strap is not essential because of the threaded engagement of the end cap 12' with the tracheal tube 26'. In use, the disposable filter element 24' is removed after removal of the screen 14'. After inserting a new filter, the screen 14' is either cleaned and replaced, or a new screen installed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved tracheal tube filter comprising:
    tubular filter holding means adapted to be inserted into an outer end portion of a tracheal tube;
    said tubular filter holding means having inner and outer ends;
    said tubular filter holding means formed from a resilient plastic material;
    filter means received in said tubular filter holding means;
    screen means disposed over said filter means;
    a lip formed at said outer end of said tubular filter holding means, said lip adapted to be received over the outer end portion of a tracheal tube;
    said lip forming an annular recess adapted to be received in frictional engagement over the outer end of a tracheal tube;
    said lip having an outwardly extending cylindrical surface provided with threads; and
    end cap means having a circular recess provided with cooperating threads for engaging said threads of said tubular filter holder lip.

2. The tracheal tube filter of claim 1, wherein said end cap means has a central aperture and said screen means is disposed in said central aperture.

3. The tracheal tube filter of claim 2, wherein said central aperture of said end cap means is circular;
    said end cap means has a circular undercut recess formed coaxially with said circular central aperture;
    said screen means being formed from a flat, circular piece of flexible screen material; and
    said screen means being removably received in said circular undercut recess.

4. The tracheal tube filter of claim 1, further comprising a loop means formed on said end cap means and a retaining cord means disposed through said loop means for receipt around a user's neck.

5. The tracheal tube filter of claim 4, wherein said retaining cord means comprises a chain.

6. The tracheal tube filter of claim 1, wherein said end cap means is formed from a precious metal and is provided with ornamentation.

7. A new and improved tracheal tube filter comprising:
    tubular filter holding means formed from a resilient plastic material adapted to be inserted into an outer end portion of a tracheal tube;
    fibrous filter means treated with a germicidal agent received in said tubular filter holding means;
    said tubular filter holding means having an outer end surface;
    a lip formed on said outer end surface of said tubular filter holding means;
    said lip forming a circular annular recess adapted to be received in frictional engagement over the outer end portion of a tracheal tube;
    said lip having an outwardly extending cylindrical surface provided with threads;
    end cap means having a circular recess provided with threads for cooperating engagement with the threads on said tubular filter holding means lip;
    said end cap means having a central circular aperture and a coaxial circular undercut recess formed coaxially with said circular aperture;
    screen means formed from a flat circular piece of resilient screen material removably received in said circular undercut recess;
    loop means formed on said end cap means;
    a retaining chain adapted to be worn around a user's neck disposed through said loop means; and
    said end cap means being formed from a precious metal and provided with ornamentation.

8. A new and improved tracheal tube filter adapted for use with a tracheal tube having an externally threaded outer end portion, comprising:
    tubular filter holding means adapted to be inserted into an outer end portion of a tracheal tube;
    said tubular filter holding means having inner and outer ends;
    fibrous filter means treated with a germicidal agent received in said tubular filter holding means;
    an inwardly extending circular flange formed on said inner end of said tubular filter holding means for retaining said fibrous filter means;
    a lip formed on said outer end of said tubular filter holding means;
    said lip forming a circular annular recess having a threaded inner wall adapted to be received in threaded engagement with the threaded outer end portion of a tracheal tube;
    end cap means formed integrally with said lip;
    said end cap means having a central circular aperture and a coaxial circular undercut recess formed coaxially with said circular aperture;
    screen means formed from a flat, circular piece of resilient screen material;
    said screen means having a circular peripheral edge removably received in said circular undercut recess; and
    said end cap means formed from a precious metal and provided with ornamentation.

* * * * *